(12) United States Patent
Hu et al.

(10) Patent No.: US 8,287,451 B2
(45) Date of Patent: Oct. 16, 2012

(54) FLEXIBLE BIOMONITOR WITH EMI SHIELDING AND MODULE EXPANSION

(75) Inventors: Ying-Chiang Hu, Taoyuan County (TW); Ting-Chen Ke, Taichung (TW); Wen-Ying Chang, Taoyuan County (TW); Chun-Hsun Chu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 887 days.

(21) Appl. No.: 12/138,638

(22) Filed: Jun. 13, 2008

(65) Prior Publication Data

US 2008/0259577 A1    Oct. 23, 2008

Related U.S. Application Data

(63) Continuation-in-part of application No. 11/132,216, filed on May 19, 2005, now abandoned.

(51) Int. Cl.
*A61B 5/00* (2006.01)

(52) U.S. Cl. .......................................... 600/301; 600/549

(58) Field of Classification Search ................. 600/301, 600/306, 549; 340/573.1; 361/749
See application file for complete search history.

(56) References Cited

U.S. PATENT DOCUMENTS

| | | | |
|---|---|---|---|
| 5,830,136 A | 11/1998 | Delonzor et al. | |
| 6,484,045 B1 | 11/2002 | Holker et al. | |
| 6,517,497 B2 * | 2/2003 | Rymut et al. | 600/538 |
| 6,934,570 B2 | 8/2005 | Kiani et al. | |
| 7,625,117 B2 * | 12/2009 | Haslett et al. | 374/111 |
| 7,656,673 B1 * | 2/2010 | Fries et al. | 361/749 |
| 2001/0047127 A1 | 11/2001 | New, Jr. et al. | |
| 2004/0242976 A1 | 12/2004 | Abreu | |
| 2005/0096513 A1 | 5/2005 | Ozguz et al. | |
| 2005/0217895 A1 | 10/2005 | Maharshak et al. | |
| 2007/0206655 A1 * | 9/2007 | Haslett et al. | 374/141 |

FOREIGN PATENT DOCUMENTS

| | | |
|---|---|---|
| CN | 1092278 | 9/1994 |
| WO | WO03065926 | 8/2003 |

OTHER PUBLICATIONS

State Intellectual Property Office of the People's Republic of China, "Office Action", Sep. 7, 2007, China.

* cited by examiner

*Primary Examiner* — Brian Szmal
*Assistant Examiner* — H. Q. Nguyen
(74) *Attorney, Agent, or Firm* — WPAT, PC; Justin King

(57) ABSTRACT

A flexible biomonitor comprises: a flexible substrate having a circuit apparatus, a hybrid sensor, a plurality of IC devices, a central processing module, a RF transmitter circuit, an antenna, and a power supply. Thereupon the flexible biomonitor can be plastered on the skin where the human body needs to be monitored to achieve the purposes of reducing occupied area, providing comfortable wear and achieve compactness, module expansion and EMI shielding. Besides, it is capable of remote real-time monitoring this signal to achieve the purpose of home care.

14 Claims, 7 Drawing Sheets

FLEXIBLE BIOMONITOR WITH EMI SHIELDING AND MODULE EXPANSION

CROSS REFERENCE TO RELATED PATENT APPLICATION

This is a continuation in part application of an application Ser. No. 11/132,216 filed on May 19, 2005, which further claims the benefit of Taiwan application Serial No. 94108277, filed Mar. 21, 2005; the subject matter of which is incorporated herein by reference.

FIELD OF THE INVENTION

The present invention relates to a flexible biomonitor with EMI shielding and module expansion, and more particularly to a flexible biomonitor using at least a pair of flexible wing circuit boards having radio frequency (RF) components being disposed thereon separated from a two-sided flexible main circuit board while being discretely coupled to the two-sided flexible main circuit board through a pair of pads attached to the two-sided flexible main circuit board so as to achieve compactness, module expansion and EMI shielding.

BACKGROUND OF THE INVENTION

According to statistic data of Frost and Sullivan business consulting firm in Year 2000, America, Western Europe, and Asia hold almost 70 percent of global medical device market, wherein Asia holds about 17 percent of global medical device market. In the mean time, the report produced by Industrial Development Bureau, Ministry of Economic Affairs, R.O.C., indicates that the growth rate of yield of global medical device from 1992 to 2002 year is 14.83%. Moreover, the growth rate of Taiwanese medical care production value is even up to 18.5%. From the facts that Taiwanese has about one half the yearly income of American while Taiwan only has one-tenth the population of America and the production value of American remote home care market is USD 40 to 70 billion, The production value of Taiwanese remote home care market is estimated to be USD 2 to 3.5 billion per year. Accordingly, the medical industry using wireless communication technology will substantially affect the future economy of Taiwan. It is expected that the developed plaster-type wireless transmission/reception module and key components thereof can assist the domestic wireless and biomedical manufacturers in mastering the business opportunity and equipping with favorable conditions and leading role for contending with overseas manufacturers.

In the meantime, according to the statistic, the marketing scale of the global medical device in the Year 2005 is estimated to be USD 192 billion with an average growth rate of 5%. The US Department of Commerce also estimates that ten newly risen markets including The Association of Southeast Asian Nations, The Chinese Economic Area (China, Taiwan, Hong Kong), South Korea, India, South Africa, Poland, Turkey, Mexico, Brazil, and Argentina will be formed in the year 2010. The amount of the medical devices imported by these ten newly risen markets will be multiplied, and the growth rate of the medical care expense of these markets will be two or three times over the developed countries. Asia area and Eastern Europe among them will have the rapidest growth rate. Regarding the domestic market of Taiwan, the medical care expense is also raising continually since Taiwanese had gradually pay more attention to the health and medical care and the Government sets the National Health Insurance Program into action. The market values of Taiwan in the years 1998 and 2000 are NTD 16.921 and 22.3 billion, respectively, and is estimated to be NTD 43 billion in the year 2005 with an average growth rate of 13.9%.

In order to enable the people with chronic disease and/or the people who require media to be able to move freely with the application preventive medicine for reducing disease and disability, the core technologies of information and communication industries are utilized to broaden the scope of the cared objects and meet the need of personalized long-term care via the borderless network such that the number of hospital visit can be reduced, and the probability of having nosocomial infection is also reduced. Accordingly, the lives of the aged persons and the person who require care become more plentiful. In order to achieve the purpose of remote home care, the real-time wireless monitoring module using the network will be the most human solution. In the mean time, with the solid foundation of wireless-related industries in Taiwan and the characteristic of short developing time required for developing the new electric medical device, it is the best time for developing the remote home care module and device. The product of the present invention is disclosed in accordance with this trend.

A physiological plaster having the wireless monitoring function is disclosed in a patent WO03065926 (also US Pat. Appl. No. 20050096513), entitled "Wearable Biomonitor with Flexible Thinned Integrated Circuit". Referring to FIG. 1, which is a block diagram of a circuitry integrated onto a thinned silicon substrate according to US Pat. Appl. No. 20050096513, the circuitry comprises a microprocessor 11, a ROM 12 for storing a program to be implemented, a RAM 13 for storing of data, and a transmitter or transceiver 14 for transmitting data by RF signals to a remote receiver. The circuitry also includes the electrodes 15 for front end analog data collection. The electrodes 15 are connected to an analog/digital converter 16 to convert the analog signals to digital signals to be processed in the microprocessor 11. Moreover, a battery 17 supplies power to the elements on the circuitry. In this cited patent, the plaster module is a single-sided plaster module. In other words, the sensor and the electronic device are mounted on the same side of the physiological plaster, which will cause the plaster to have the following drawbacks: (1) the area of the physiological plaster cannot be reduced; (2) the wear is less comfortable because of perspired sweat from the body; (3) the electronic device cannot be properly protected; and (4) EMI shielding is not available so that the signal transmitted from the physiological plaster may be easily interfered. Moreover, FIG. 2 shows a method for producing via connections in a flexible printed circuit according to US Pat. Appl. No. 20050217895. In FIG. 2, a thin, flexible, non-conductive substrate 20 is fashioned with a set or array of tiny holes 22 in the location where a first conductive line 24 and a second conductive line 28 are to overlap on opposing sides of substrate 20 and make an electrical connection, or in the location where the substrate 20 is subject to mechanical stress and anchoring of the conductive line is needed. Moreover, a conductive material such as a conductive paint 26 is applied to a first side of the substrate 20 to form the first conductive line 24. However, in this cited patent, the conductive lines 24 and 28 are formed by electroplating or chemical deposition to form metal layers on the polymer substrate and are then connected by the conductive paint 26. This requires complicated manufacturing processing.

Therefore, there is demand in providing using at least a pair of flexible wing circuit boards having radio frequency (RF) components being disposed thereon separated from a two-sided flexible main circuit board while being discretely coupled to the two-sided flexible main circuit board through a pair of pads attached to the two-sided flexible main circuit board so as to achieve compactness, module expansion and EMI shielding.

SUMMARY OF THE INVENTION

The primary object of the invention is to provide a flexible biomonitor that is a system integrated with a two-sided flexible main circuit board, wherein the system integrates radio frequency (RF) components with a hybrid sensor to form a plaster-sized module capable of attaching to the skin of a tested area for sensing and monitoring temperature and a plurality of physiological signals.

Another object of the present invention is to provide a flexible biomonitor, in which a plurality of through holes for conducting electricity are formed on the two-sided flexible main circuit board enabling the electronic device and the sensor to be mounted respectively on the two sides of the two-sided flexible main circuit board for reducing occupied area and providing comfortable wear.

A further object of the present invention is to provide a flexible biomonitor capable of transmitting a hybrid signals monitored thereby wirelessly using RFID technology. Accordingly, the purpose of home care is achieved by use of the network system of the medical center to perform the personalized remote real-time monitoring and to reduce the probability of having nosocomial infection by reducing the number of hospital visits of patients, aged persons, and children. Thereupon the medical quality is improved.

In order to achieve the aforementioned objects, the present invention provides a flexible biomonitor comprising:

a flexible substrate having a circuit apparatus, formed on the flexible substrate, the circuit apparatus having a circuit layout mounted thereon and further comprising:
  a bottom circuit layer, connected with one side of the flexible substrate; and
  a top circuit layer connected with the other side of the flexible substrate, and being electrically connected with the bottom circuit layer;
a hybrid sensor being disposed on the bottom circuit layer and being capable of sensing at least a temperature signal and a physiological phenomenon to generate a signal;
a plurality of IC devices disposed on the top circuit layer and being capable of performing signal processing on the signal to generate a processed signal;
a central processing module disposed on the top circuit layer and being capable of performing signal processing on the processed signal to generate a hybrid signal;
a pair of flexible wing circuit boards having a RF transmitter circuit and an antenna disposed thereon, each disposed separated from the circuit apparatus while being discretely coupled to the circuit apparatus through a pair of pads attached to the circuit apparatus, to transmit the hybrid signal in a wireless manner; and
a power supply electrically connected with the circuit apparatus for supplying electric power to the circuit apparatus, the hybrid sensor, the IC devices, the central processing module, the RF transmitter circuit and the antenna.

DESCRIPTION OF THE PREFERRED EMBODIMENT

The above-mentioned features and advantages of this invention, and the manner of attaining them, will become more apparent and the invention will be better understood by reference to the following description of embodiments of the invention taken in conjunction with the drawings. But, the scope of the present invention is not limited to the drawings.

Figure 1:
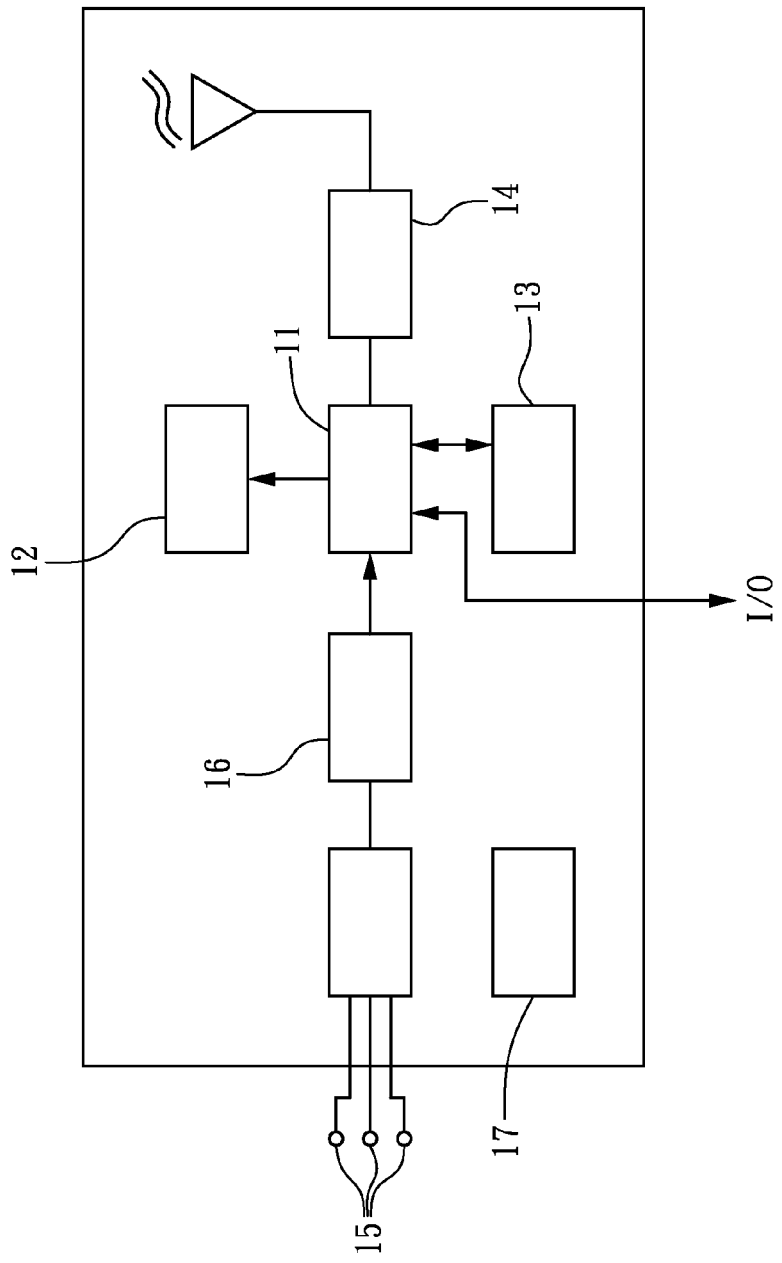
FIG. 1 is a block diagram of the circuitry integrated onto a thinned silicon substrate according to US Pat. Appl. No. 20050096513.
Figure 2:
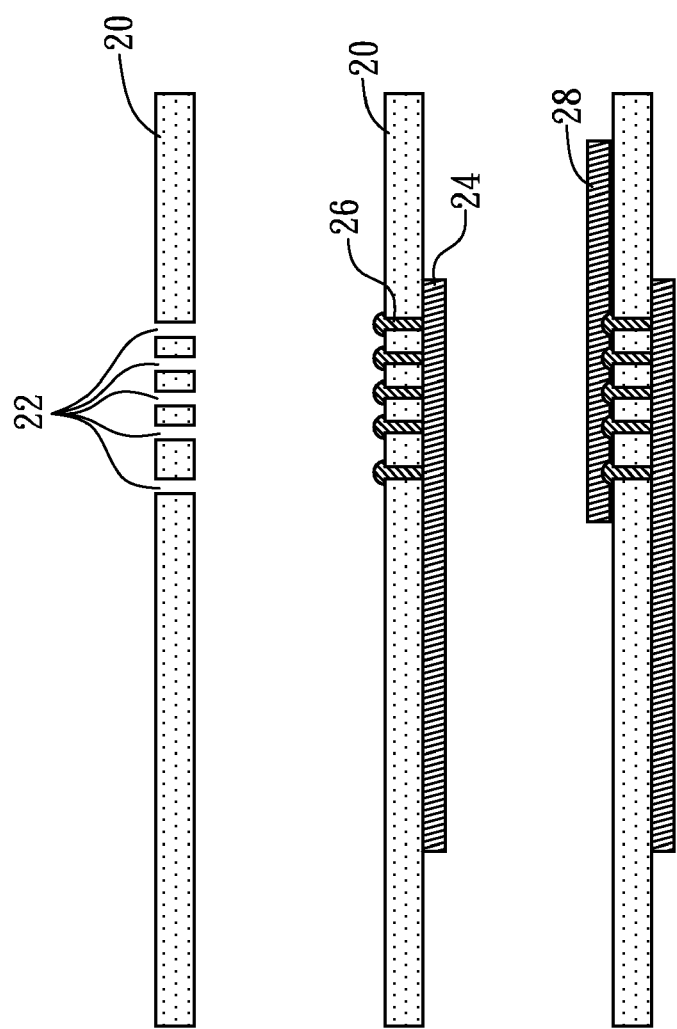
FIG. 2 shows a method for producing via connections in a flexible printed circuit according to US Pat. Appl. No. 20050217895.
Figure 3A:
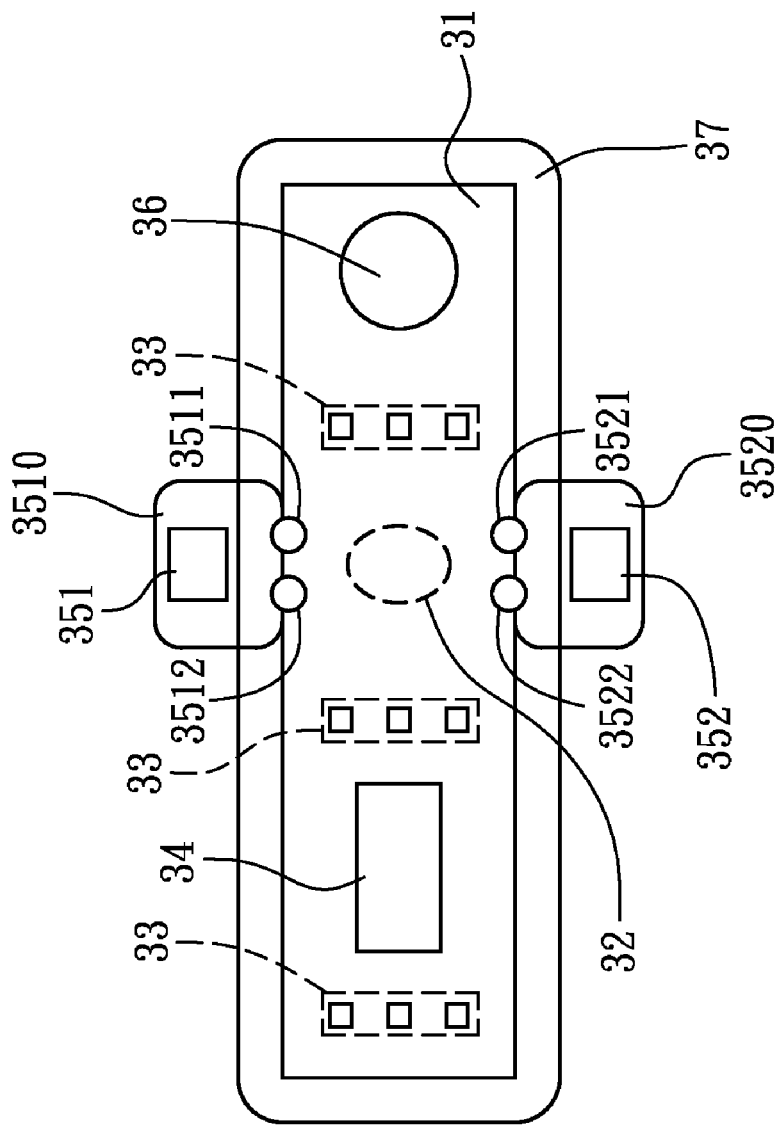
FIG. 3A is a top view showing a flexible biomonitor of the present invention.
Figure 4:
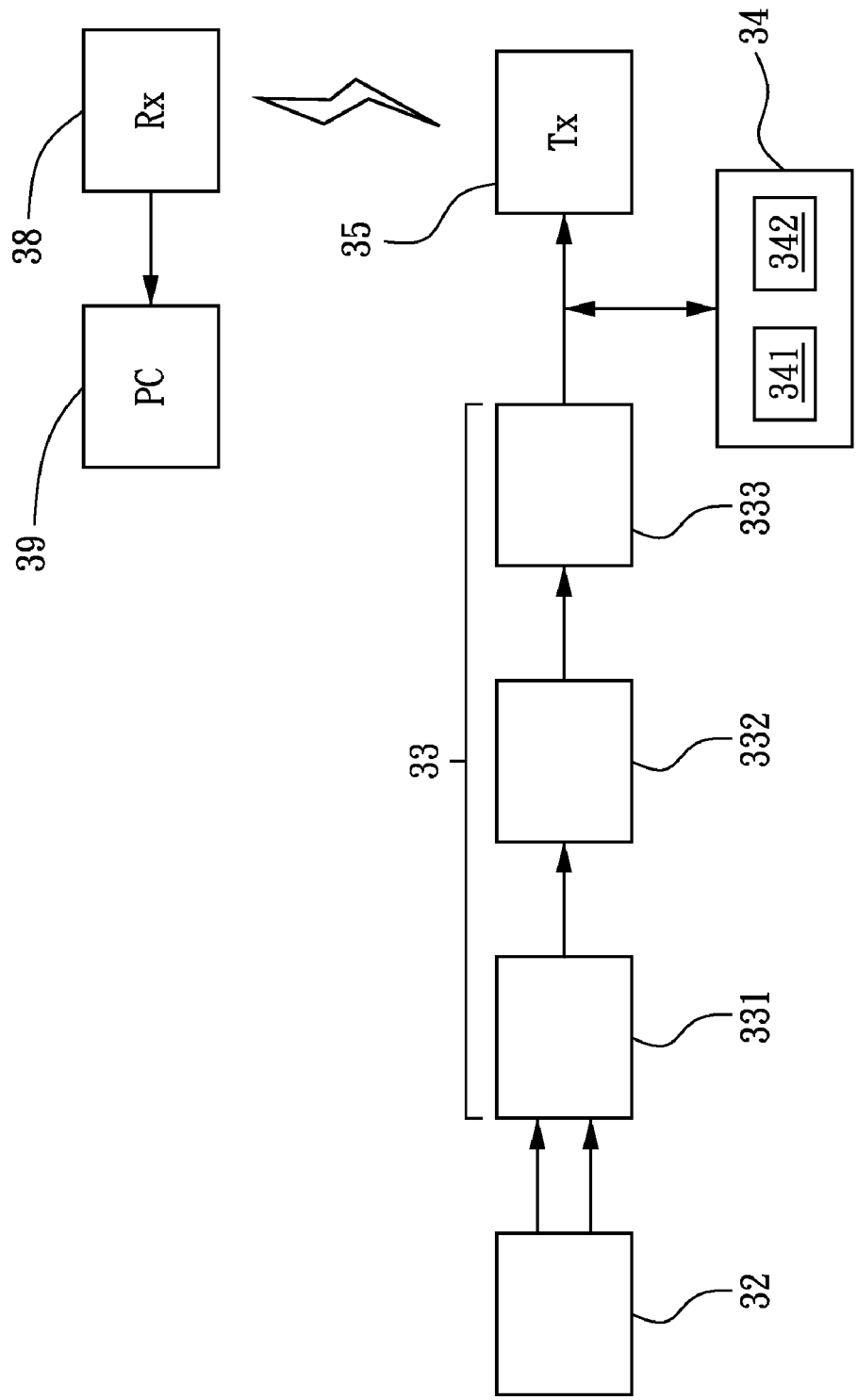
FIG. 4 is a functional diagram showing the flexible biomonitor in accordance with one embodiment of the present invention.

Referring to FIG. 3A and FIG. 4, a top view and a functional diagram of a flexible biomonitor of one embodiment of the present invention are shown, respectively. The flexible biomonitor comprises a flexible substrate 31, a hybrid sensor 32, a plurality of IC devices 33, a central processing module 34, a RF transmitter circuit 351, an antenna 352, a power supply 36, and a package 37.

Figure 3B:
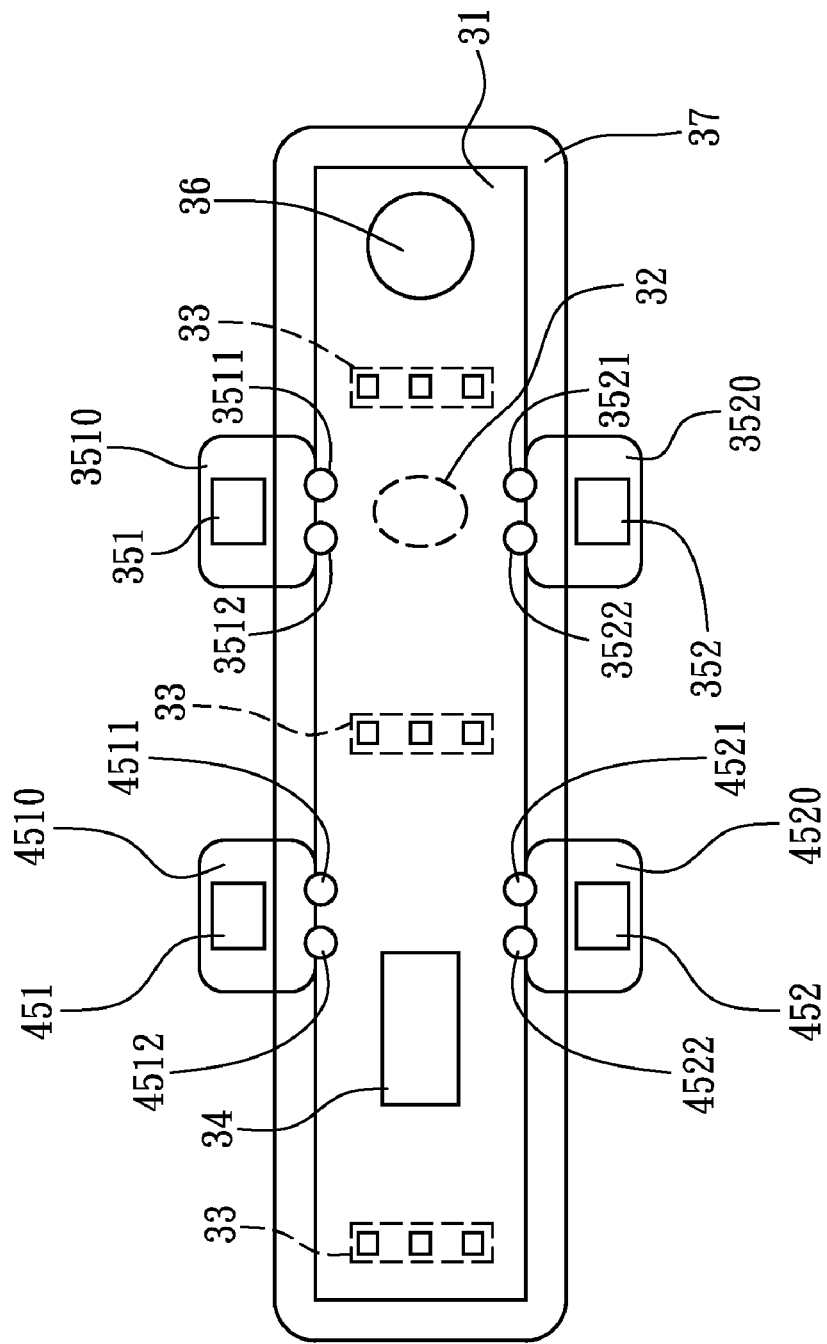
FIG. 3B is a top view showing another flexible biomonitor of the present invention.
Figure 3C:
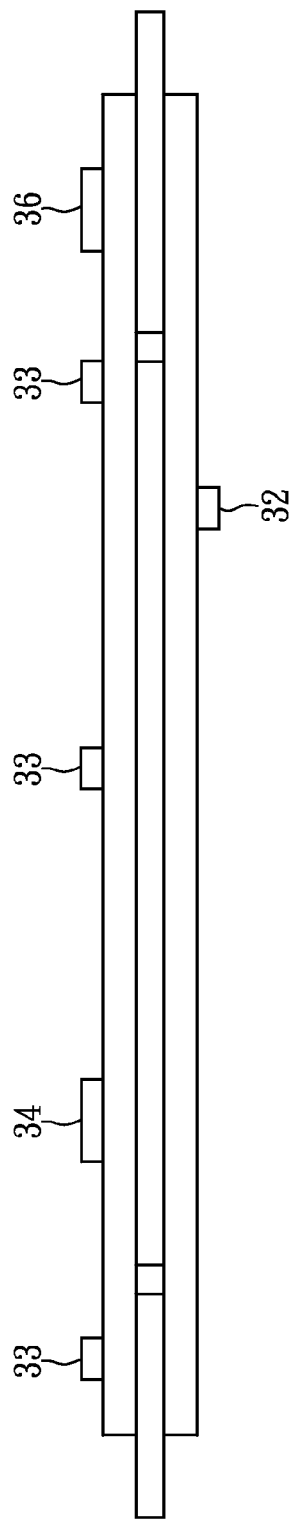
FIG. 3C is a side view showing another flexible biomonitor of the present invention.

The flexible substrate 31 has a circuit apparatus formed on the flexible substrate 31. The circuit apparatus has a circuit layout (not shown) mounted thereon. More particularly, the circuit apparatus comprises: a bottom circuit layer, connected with one side of the flexible substrate 31; and a top circuit layer connected with the other side of the flexible substrate 31, and being electrically connected with the bottom circuit layer. FIG. 3C shows a side view of one such configuration of components on a set of circuit layers in accordance with the invention.

The flexible substrate 31 comprises several through holes formed thereon, wherein the through holes are formed by the through hole manufacture process of the circuit board and mounted to penetrate through the flexible substrate 31. These through holes are filled with a conducting material for providing electrical connection.

The hybrid sensor 32 is disposed on the bottom circuit layer and is capable of sensing at least a temperature signal and a physiological phenomenon of the human body for generating a signal (not shown).

The plurality of IC devices 33 are disposed on the top circuit layer and is capable of performing signal processing on the signal to generate a processed signal. More particularly, these IC devices 33 are a filter 331, an amplifier 332 and an analog-to-digital converter (ADC) 333 to perform signal amplifying, signal filtering, analog/digital signal conversion, signal encoding, signal decoding, etc.

The central processing module 34 is disposed on the top circuit layer and is capable of performing signal processing on the processed signal to generate a hybrid signal. More particularly, the central processing module 34 comprises a memory module 341 and a micro-processor 342. The memory module 341 comprises a RAM and a flash ROM.

Each of the RF transmitter circuit 351 and the antenna 352 (as Tx 35 in FIG. 4) is disposed on a flexible wing circuit layer 3510/3520 separated from the circuit apparatus while being discretely coupled to the circuit apparatus through a pair of pads (3511, 3512 and 3521, 3522) attached to the circuit apparatus, to transmit the hybrid signal in a wireless manner. The pads are attached to the circuit apparatus using a conductive adhesive. More particularly, for the RF transmitter circuit 351, one pad 3511 is coupled to the top circuit layer while the other pad 3512 is coupled to the bottom circuit layer. Similarly, for the antenna 352, one pad 3521 is coupled to the top circuit layer while the other pad 3522 is coupled to the bottom circuit layer. Therefore, parasitic noise is grounded into the bottom circuit layer to prevent EMI.

The hybrid signal is transmitted to a RFID receiver 38 and then processed in an electronic device such as a personal computer 39 for real-time monitoring the temperature signal and the physiological phenomenon.

The power supply 16 is electrically connected with the top circuit layer for supplying the electric power to the circuit apparatus, the hybrid sensor 32, the IC devices 33, the central processing module 34, the RF transmitter circuit 351 and the antenna 352.

Moreover, the package 17 covers the flexible substrate 11, the circuit apparatus, the hybrid sensor 32, the IC devices 33, the central processing module 34 and the power supply 36 to protect the flexible biomonitor from moisture and dust pollution and simultaneously to provide a better feel when the flexible biomonitor touches the skin (not shown).

In the present invention, the number of the flexible wing circuit board can be increased. For example, as shown in FIG. 3B, the flexible biomonitor of the present invention further comprises a pair of additional flexible wing circuit boards 4510 and 4520, each having an additional hybrid sensor 451 and 452 disposed thereon. Similarly, the additional flexible wing circuit boards 4510 and 4520 are discretely coupled to the circuit apparatus through a pair of pads (4511, 4512 and 4521, 4522) attached to the circuit apparatus. The additional hybrid sensors 451 and 452 are capable of sensing at least a temperature signal and a physiological phenomenon to generate a signal. Therefore, the flexible biomonitor of the present invention provides module expansion when it is required that the number of hybrid sensors is increased. The pads (4511, 4512 and 4521, 4522) are attached to the circuit apparatus using a conductive adhesive. The present invention is advantageous because the precision is enhanced by multi-point sensing and the additional hybrid sensors are immune from EMI noise.

More particularly, the hybrid sensor disposed on the bottom side substrate can detect bioelectric signals, pressure signal, vibrated signal, light reflected signal moisture signals and the other bio sensor signal. The physiological interface element can be mounted on the bottom side substrate. Furthermore, it is to be understood that while in the preferred embodiment, the sensor module can be used to detect physiological characteristics such an EKG (from the heart), EEG (from the brain), blood pressure, sPO2, respiratory vibration, urine damp, blood sugar and so on.

In the present invention, the flexible wing circuit boards having elements or modules thereon can be attached to the flexible main circuit board through pads. More particularly, the pads are formed of a conductive adhesive and pressed onto the flexible main circuit board after alignment.

Figure 5:
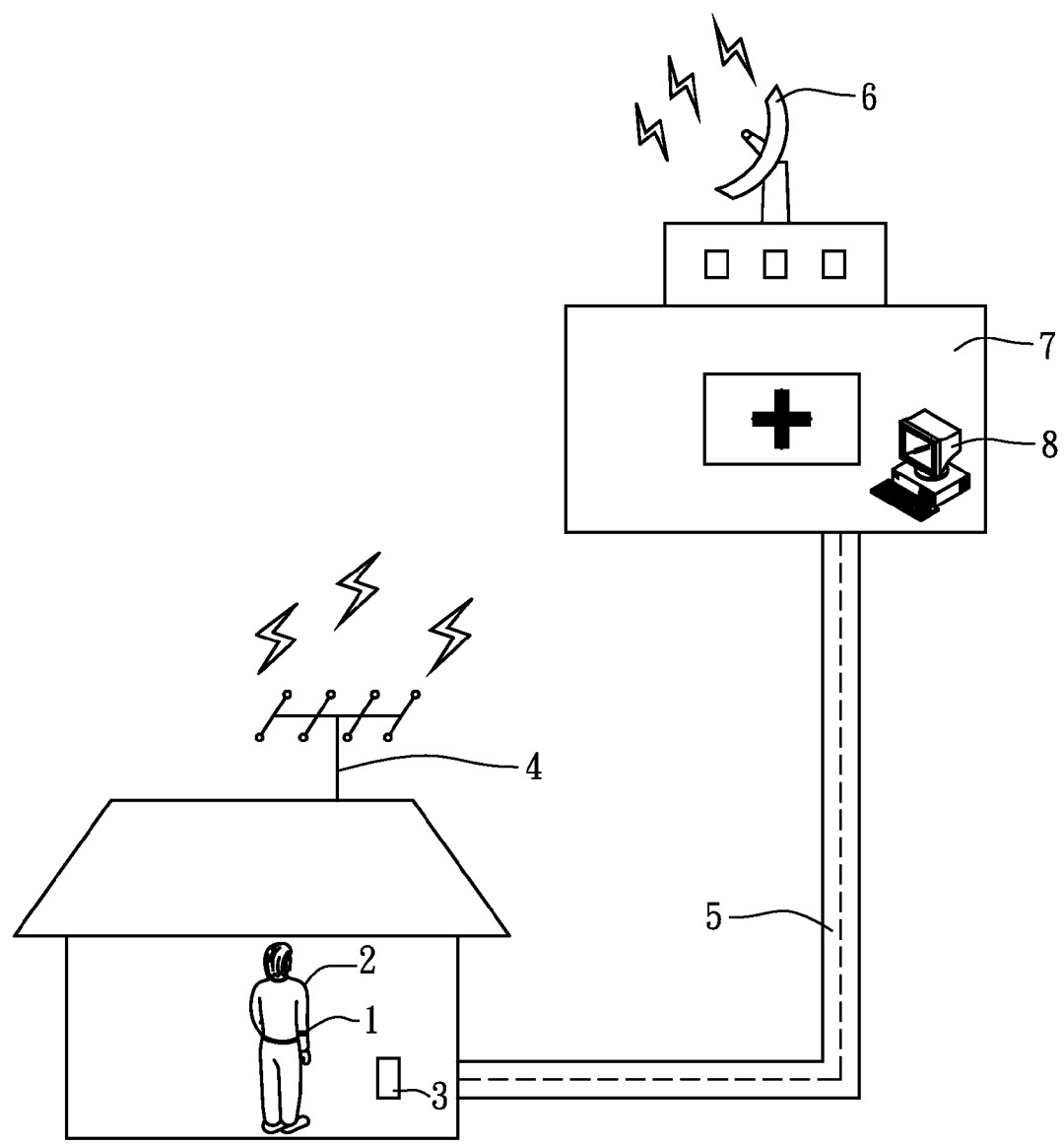
FIG. 5 is a schematic view showing an example of use of the flexible biomonitor of the present invention.

FIG. 5 is a schematic view showing an example of use of the flexible biomonitor of the present invention. As shown in FIG. 5, the user (patient) 2 wears the flexible biomonitor 1 of the present invention. When the flexible biomonitor 1 obtains a temperature signal and a physiological phenomenon (not shown) of the user 2, it converts the temperature signal and the physiological phenomenon into a signal carrier wave (not shown) and transmits the signal carrier wave to the RFID receiver 3 mounted in the user's house. Next, the RFID receiver 3 further transmits the signal carrier wave to a carrier wave receiver 6 mounted in a medical station 7. Thereafter, the carrier wave receiver 6 converts the signal carrier wave into digital data, which is shown on a monitor 8 by image. Alternatively, the RFID receiver 3 converts the signal carrier wave into a general digital signal (not shown), and then the digital signal is transmitted to the monitor 8 of the medical station 7 via the Ethernet 5 for showing the digital signal by image. Accordingly, the purpose of remote monitoring is achieved.

In the present invention, these circuit layers can be electrically connected by use of the copper conducting wires applied to the traditional surface or the through holes penetrated through the flexible substrate. Thereupon the occupied area of the flexible substrate is efficiently saved and the size of the flexible biomonitor is reduced. In the meantime, the IC devices are all kinds of active and passive IC devices capable of amplifying signal, filtering signal, converting analog/digital signal, encoding signal, decoding signal, etc. The hybrid sensor comprises sensing electrodes, capable of sensing a temperature signal, bioelectric signals, pressure signal, vibrated signal, light reflected signal moisture signals, the other biosensor signal of physiological phenomenon to generate a signal Besides, the power supply disclosed in this preferred embodiment of the present invention is a flexible battery and/or a rechargeable battery, and the monitored physiological signal is the user's heartbeat frequency, body temperature, etc. The flexible substrate is made of a material such as polyimide (PI), polyvinyl chloride (PVC), polyvinyl alcohol (PVA), etc. The package is made of a material such as polydimethylsiloxane (PDMS), polyurethane (PU), epoxy, etc.

In the present invention, the package can completely cover the flexible substrate, the bottom circuit layer, the top circuit layer, the paste wing circuit layers, the RFID sensing chip, the antenna circuit, the transmitter circuit, and the power supply. Nevertheless, when the hybrid sensor comprises sensing electrodes that need to touch the user's skin directly, the package covers the flexible substrate, the paste wing circuit layers, the bottom circuit layer, the top circuit layer, the transmitter circuit, the RFID sensing chip, the antenna, and the power supply and exposes the hybrid sensor. Accordingly, the hybrid sensor is allowed to touch the user's skin directly.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A flexible biomonitor configured for sensing and monitoring temperature and a plurality of physiological phenomenon signals, comprising:
   a flexible substrate having a circuit apparatus, formed on the flexible substrate, the circuit apparatus having a circuit layout mounted thereon and further comprising:
   a bottom circuit layer, connected with one side of the flexible substrate;
   a top circuit layer connected with the other side of the flexible substrate, and being electrically connected with the bottom circuit layer;
   a plurality of through holes, wherein each through hole passes through the flexible substrate and is filled with a conducting material for enabling electric current to pass between components on the top circuit layer and components on the lower circuit board;
a hybrid sensor being disposed on the bottom circuit layer configured for sensing at least a temperature signal and a physiological phenomenon to generate a signal indicative of the sensed temperature and physiological phenomenon;
a plurality of IC devices disposed on the top circuit layer configured for performing signal processing on the signal to generate a processed signal indicative of at least the sensed temperature and physiological phenomenon;
a central processing module disposed on the top circuit layer configured for performing signal processing on the processed signal to generate a hybrid signal for wireless transmission of said hybrid signal;
at least a pair of flexible wing circuit boards, each pair of flexible wing circuit boards having at least a RF transmitter circuit or an antenna disposed thereon, wherein each pair of flexible wing circuit boards are disposed separated from the circuit apparatus while being discretely coupled to the circuit apparatus through a pair of pads attached to the circuit apparatus using conductive adhesive, to transmit the hybrid signal to a remote receiver by said wireless transmission, wherein a first pad of each pair of pads is coupled to the top circuit layer and a second pad of each pair of pads is coupled to the bottom circuit layer; and
a power supply electrically connected with the circuit apparatus for supplying electric power to the circuit apparatus, the hybrid sensor, the IC devices, the central processing module, the RF transmitter circuit and the antenna.

2. The flexible biomonitor of claim 1, further comprising a package, covering the flexible substrate, the circuit apparatus, the hybrid sensor, the IC devices, the central processing module, and the power supply.

3. The flexible biomonitor of claim 2, wherein the package is made of a material selected from a group consisting of polydimethylsiloxane (PDMS), polyurethane (PU), and epoxy.

4. The flexible biomonitor of claim 1, wherein the bottom circuit layer is electrically connected with the top circuit layer via the through holes.

5. The flexible biomonitor of claim 1, wherein the IC devices are active IC devices.

6. The flexible biomonitor of claim 1, wherein the IC devices are passive IC devices.

7. The flexible biomonitor of claim 1, wherein the hybrid sensor comprises sensing electrodes.

8. The flexible biomonitor of claim 1, wherein the physiological phenomenon is heartbeat frequency.

9. The flexible biomonitor of claim 1, wherein the signal processing performed by the plurality of IC devices and the central processing module includes at least a procedure selected from the group consisting of signal amplifying, signal filtering, analog/digital signal converting, signal encoding, and signal decoding.

10. The flexible biomonitor of claim 1, wherein the power supply is a flexible battery.

11. The flexible biomonitor of claim 1, wherein the power supply is a rechargeable battery.

12. The flexible biomonitor of claim 1, wherein the flexible substrate is made of a material selected from a group consisting of polyimide (PI), polyvinyl chloride (PVC), and polyvinyl alcohol (PVA).

13. The flexible biomonitor of claim 1, wherein the signal is received by a wireless reader.

14. The flexible biomonitor of claim 1, further comprising at least an additional flexible wing circuit board having at least an additional hybrid sensor disposed thereon, the additional hybrid sensor being capable of sensing at least a temperature signal and a physiological phenomenon to generate a signal.

* * * * *